(12) United States Patent
Schattke et al.

(10) Patent No.: US 6,305,214 B1
(45) Date of Patent: Oct. 23, 2001

(54) GAS SENSOR AND METHODS OF FORMING A GAS SENSOR ASSEMBLY

(75) Inventors: Nathan Schattke, Yorkville; Dennis Martell, Naperville, both of IL (US)

(73) Assignee: Sensor Tek, LLC, Wheeler, IN (US)

( * ) Notice: Subject to any disclaimer, the term of this patent is extended or adjusted under 35 U.S.C. 154(b) by 0 days.

(21) Appl. No.: 09/383,341

(22) Filed: Aug. 26, 1999

(51) Int. Cl.⁷ .................................................. G01N 27/49
(52) U.S. Cl. ........................ 73/31.05; 73/23.2; 73/431; 204/412; 204/415
(58) Field of Search .................................. 204/194, 411, 204/412, 415, 400; 73/23.2, 31.05, 431

(56) References Cited

U.S. PATENT DOCUMENTS

| | | | |
|---|---|---|---|
| 3,622,488 | 11/1971 | Chand et al. | 204/195 |
| 3,776,832 | 12/1973 | Oswin et al. | 204/195 R |
| 3,878,080 | 4/1975 | Luck | 204/195 P |
| 3,909,386 | 9/1975 | Oswin et al. | |
| 4,036,724 | 7/1977 | Binder et al. | 204/195 R |
| 4,171,253 | 10/1979 | Nolan et al. | 204/195 S |
| 4,329,214 | 5/1982 | Spritzer et al. | |
| 4,478,704 | 10/1984 | Miyoshi et al. | 204/412 |
| 4,525,266 | 6/1985 | Schmidt et al. | 204/412 |
| 4,621,035 | 11/1986 | Bruder | 429/152 |
| 4,688,021 | 8/1987 | Buck et al. | 340/521 |
| 4,695,361 | 9/1987 | Grady | 204/415 |
| 4,717,633 | 1/1988 | Hauser | 429/209 |
| 4,767,994 | 8/1988 | Hopkins et al. | 324/438 |
| 4,816,355 | 3/1989 | Kulibert et al. | 429/174 |
| 4,874,500 | 10/1989 | Madou et al. | 204/412 |
| 4,900,643 | 2/1990 | Eskra et al. | 429/241 |
| 4,948,681 | 8/1990 | Zagrodnik et al. | 429/34 |
| 5,126,035 | 6/1992 | Kiesele et al. | 204/415 |
| 5,173,166 | 12/1992 | Tomantschger et al. | 204/412 |
| 5,183,550 | 2/1993 | Mattiessen | 204/415 |
| 5,250,171 | 10/1993 | Warburton et al. | 204/431 |
| 5,281,324 | 1/1994 | Kiesele et al. | 204/415 |
| 5,302,274 | 4/1994 | Tomantschger et al. | 204/412 |
| 5,314,605 | 5/1994 | Matthiessen | 204/415 |
| 5,331,310 | 7/1994 | Stetter et al. | 340/632 |
| 5,336,390 | 8/1994 | Busack et al. | 204/431 |
| 5,573,648 | 11/1996 | Shen et al. | 204/412 |
| 5,914,019 | * 6/1999 | Dodgson et al. | 204/415 |
| 5,987,965 | * 11/1999 | Martell et al. | 73/31.06 |
| 6,099,708 | * 8/2000 | Mallory et al. | 204/412 |

FOREIGN PATENT DOCUMENTS

| | | |
|---|---|---|
| 4025635 | 2/1991 | (DE) . |
| 0298570 | 1/1989 | (EP) . |
| 0762116 | 3/1997 | (EP) . |
| 61147145-A | * 7/1986 | (JP) .................................. 73/31.05 |

OTHER PUBLICATIONS

Japanese Patent Abstract No. 62218852, dated Sep. 26, 1987.
Japanese Patent Abstract No. 4134234, dated May 8, 1992.
Blurton et al., "Controlled–Potential Electrochemical Analysis of Carbon Monoxide," American Laboratory, Jul. 1974, 5 pages.
Bay et al., "Electrochemical Technique for the Measurement of Carbon Monoxide," Analytical Chemistry, vol. 46, Oct. 1974, pp. 1837–1839.

* cited by examiner

Primary Examiner—Hezron Williams
Assistant Examiner—Michael Cygan
(74) Attorney, Agent, or Firm—Marshall, Gerstein & Borun

(57) ABSTRACT

A gas sensor assembly is provided with a non-conductive housing portion and a plurality of conductive housing portions, each of which are conductively separated from each other, and the conductive housing portions are composed of a conductive plastic material. A gas-sensing agent is disposed in a receptacle formed in the housing, and a plurality of electrodes are disposed in conductive contact with the gas-sensing agent. The gas sensor has an electrode support sheet with a plurality of electrodes formed thereon, and a seal is formed between the electrode support sheet and the housing, the seal being formed by the sealing of a portion of one of the electrodes to a portion of the housing.

7 Claims, 4 Drawing Sheets

GAS SENSOR AND METHODS OF FORMING A GAS SENSOR ASSEMBLY

BACKGROUND OF THE INVENTION

The present invention is directed to a gas sensor used to detect the presence of gases, such as carbon monoxide.

Many commercially available gas sensors are of the amperometric type having two or more electrodes in which a catalytically active metal is fixed to a porous substrate. The porous substrate may operate as a gas permeable membrane and structural support for the electrode. The electrodes are located on the inside surface of the membrane where they make contact with an electrolyte such as sulfuric acid. External circuitry maintains one of the electrodes, the working electrode, at a selected electrical potential with respect to one of the other electrodes during operation.

When the gas of interest diffuses through the porous membrane to reach the working electrode, the diffused gas is oxidized or reduced at the interface of the working electrode and the electrolyte. That reaction generates an electrical current that is proportional to the concentration of the gas. In some cases, the gas of interest reacts with another chemical which, in turn, is oxidized or reduced at the electrode. In some cases, sensors are of a galvanic design wherein a metal such as lead is oxidized to provide the opposite current to that occurring at the working electrode.

In the prior art, the sensors were connected to the external circuit through wires. For example, a platinum contact wire was connected to the catalytically active electrode and passed through the sensor body to an external contact. Since most sensors contain a corrosive, liquid electrolyte, a difficulty with sensors has been providing secure electrical contact with the electrodes while maintaining an electrolyte-tight seal at the location where the conductor passes through the sensor body. In the prior art, seals around conductors have included Teflon gaskets. In other methods, the seal has been made of thermoplastic material or epoxy resin.

U.S. Pat. No. 5,744,697 to Martell, et al. discloses a gas sensor of the type described above. The Martell, et al. gas sensor has a plastic housing composed of a plurality of conductive housing portions integrally formed with a plurality of non-conductive housing portions. The housing has a receptacle disposed therein, and a gas-sensing agent is provided in the receptacle. A support sheet that has a plurality of electrodes formed thereon is disposed above the receptacle wherein electrical contact is made with electrodes to the conductive plastic portion, and a wick disposed in the receptacle causes the gas-sensing agent to maintain electrolytically conductive contact with the electrodes formed on the support sheet inside the sensor assembly.

SUMMARY OF THE INVENTION

In one aspect, the invention is directed to a gas sensor assembly having a housing with a receptacle formed therein. The housing has a non-conductive housing portion and a plurality of conductive housing portions, each of which is conductively separated from each other, with the conductive housing portions being composed of a conductive plastic material. A gas-sensing agent is disposed in the receptacle, and a plurality of electrodes are disposed in conductive contact with the gas-sensing agent and the conductive housing portions. The gas sensor housing has a conductive agent disposed on an area that contacts a first of the conductive housing portions and a conductive agent disposed on an area that contacts a second of the conductive housing portions. A first conductor is disposed in conductive contact with the conductive agent on the area on the first conductive housing portion, and a second conductor is disposed in conductive contact with the conductive agent on the area on the second conductive housing portion to complete the connection of the sensor to the electrical circuit.

The conductive agent may comprise a mixture of conductive ink and an adhesive, and more particularly, the conductive agent may comprise a mixture of about 15% to about 25% by volume of a conductive ink, about 15% to about 25% by volume of an adhesive, and about 50% to about 70% by volume of a thinner. This type of conductive agent may be spread on the outside of the conductive housing portions to facilitate electrical connection to the circuitry.

The invention is also directed to a method of forming a gas sensor assembly having a housing with a non-conductive housing portion and a plurality of conductive housing portions composed of conductive plastic material. The method includes the steps of: (a) forming the housing to have the non-conductive housing portion and the conductive housing portions, (b) applying a conductive agent comprising a mixture of a conductive ink and an adhesive to an area on a first of the conductive housing portions and to an area on a second of the conductive housing portions, (c) placing a contact surface of the first conductor in conductive contact with the conductive agent on the area on the first conductive housing portion, and (d) placing a contact surface of the second conductor in conductive contact with the conductive agent on the area on the second conductive housing portion.

In another aspect, the invention is directed to a gas sensor assembly with a non-conductive housing portion and a plurality of conductive housing portions, each of which are formed so that areas are conductively separated from each other, and the conductive housing portions are composed of a conductive plastic material. A gas-sensing agent is disposed in a receptacle formed in the housing, and a plurality of electrodes are disposed in conductive contact with the gas-sensing agent and the conductive housing portions. The gas sensor has an electrode support sheet with a plurality of electrodes formed thereon, and a seal is formed between the electrode support sheet and the housing, the seal being formed by the sealing of a portion of one of the electrodes to a portion of the housing.

The invention is also directed to a gas sensor assembly having a housing with a non-conductive housing portion and a plurality of conductive housing portions, each of which are conductively separated from each other, and the conductive housing portions are composed of a conductive plastic material. A gas-sensing agent is disposed in a receptacle in the housing, and a plurality of electrodes are disposed in conductive contact with the gas-sensing agent. The gas sensor has an electrode support sheet with a plurality of electrodes formed thereon, a seal is formed between the electrode support sheet and the housing, the seal being formed by the sealing of a portion of one of the conductive housing portions to the electrode support sheet.

In a further aspect, the invention is directed to a method of forming an electrode sheet for a gas sensor assembly. The method includes the steps of: (a) forming a support sheet having a first side and a second side, (b) applying a liquid electrode solution to a plurality of different areas on the first side of the support sheet, and then (c) subjecting the second side of the support sheet to a reduced pressure in order to pull the liquid electrode solution disposed on the first side of the support sheet towards the second side of the support sheet.

In another aspect, the invention is directed to a gas sensor assembly having a housing with a receptacle formed therein, a gas-sensing agent disposed in the receptacle, a wick disposed within the receptacle and being impregnated with the gas-sensing agent, and a plurality of conductive patterns formed on a surface of the wick, each of the conductive patterns extending from an interior portion of the wick to a peripheral portion of the wick.

The invention is also directed to a method of forming a gas sensor assembly which includes the steps of: (a) forming a wick composed of a gas sensing agent-adsorbent material having a first side and a second side, (b) applying a liquid electrode solution to a plurality of different areas on the first side of the wick, (c) subjecting the second side of the wick to a reduced pressure in order to pull the liquid electrode solution disposed on the first side of the wick towards the second side of the wick, and (d) incorporating the wick in a gas sensor so that the wick is in contact with a gas-sensing agent disposed in the gas sensor.

In a further aspect, the invention is directed to a gas sensor assembly having a housing with a receptacle formed therein, a gas-sensing agent disposed in the receptacle, a plurality of electrodes, a wick disposed within the receptacle formed in the housing and having an elongate portion and a flat portion in contact with the elongate portion, the wick causing the gas-sensing agent to be disposed in contact with the electrodes, and a wick support disposed within the receptacle. The wick support has a first portion which supports the flat portion of the wick and a second portion which supports the elongate portion of the wick. The first portion of the wick support may be generally flat, and the second portion of the wick support may comprise a hollow tube in which the elongate portion of the wick is disposed.

The features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 8 illustrates a portion of a vacuum deposition apparatus that may be used in the manufacture of a gas sensor with a portion of a second embodiment of a gas sensor disposed there in;

DETAILED DESCRIPTION OF THE PREFERRED EMBODIMENTS

Figure 1:
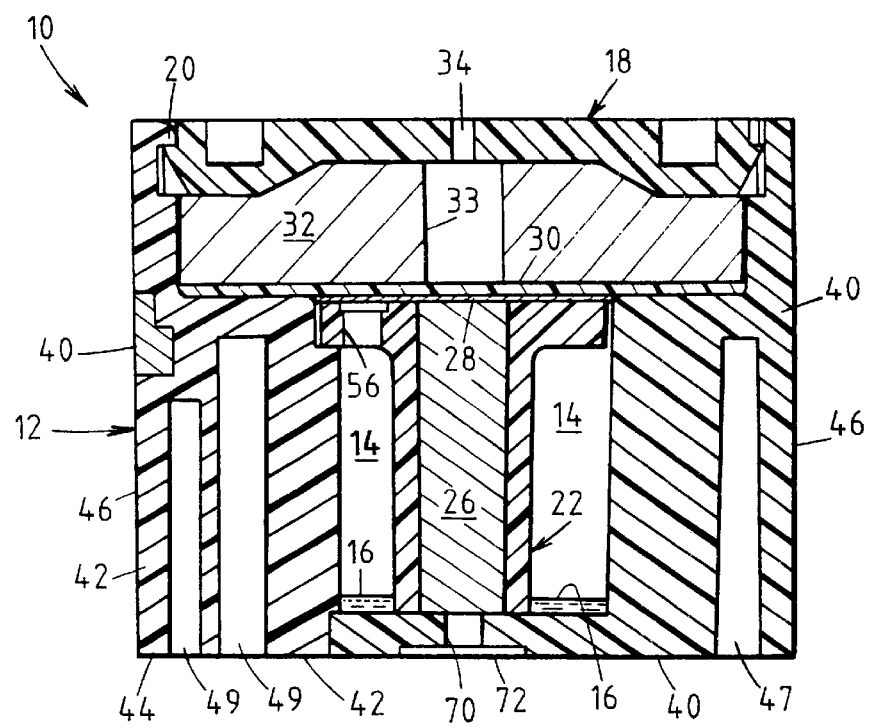
FIG. 1 is a cross-sectional view of a first embodiment of a gas sensor in accordance with the invention.

A first embodiment of a gas sensor 10 in accordance with the invention is illustrated in FIG. 1. The sensor 10 has a housing 12, which is generally cup-shaped (see also FIG. 3) in which a cylindrically shaped receptacle 14 for the storage of an electrolyte or gas-sensing agent 16 is formed. A snap-fit cover 18 is retained on the top of the housing 12 via a plurality of tabs 20 integrally formed with the housing 12.

A wick support 22 is disposed within the receptacle 14. The wick support 22 has a central cylindrical bore 24 (FIG. 5) formed therein in which a cylindrically shaped cloth wick portion 26 is disposed. The top of the wick support 22 supports a circularly shaped flat wick portion 28 that makes physical contact with the top of the wick portion 26. The housing 12, the cover 18, and the wick support 22 may be composed of plastic, such as polypropylene.

A flat circular electrode support element, in the form of a plate or sheet 30, is disposed on top of the flat wick portion 28, and a channel member 32 is disposed on top of the electrode support sheet 30 and compressed by the cover 18. The electrode support sheet 30 may comprise a plastic substrate composed of polytetrafluoroethylene (PTFE), such as Teflon® PTFE. The cover 18 has an opening or sensing hole 34 formed therein so as to expose the interior of the gas sensor 10 to the ambient atmosphere to be sensed.

The channel member 32, which may comprise foam rubber, has a central channel or bore 33 formed therein. The central bore 33 allows passage of gas to be sensed to the central area of the electrode support sheet 30 (where a working electrode is disposed) while preventing passage of gas to the outer portions of the electrode support sheet 30 (where other electrodes such as counter and reference electrodes are disposed). The channel member 32 also acts to maintain the electrode support sheet 30 in a generally planar shape. The electrode support sheet 30 allows passage therethrough of the gaseous atmosphere to be sensed.

The wick portions 26, 28 maintain the underside of the electrode support sheet 30 (which has three electrodes formed thereon) in fluid contact with the gas-sensing agent 16. The wick portion 26 may be composed of glass paper or glass wool or similar substances, and the wick portion 28 may be composed of one or more layers of filter paper, such as type GF/B filter paper commercially available from Whatman. Where the gas sensor 10 is used to detect the presence of carbon monoxide, the gas-sensing agent 16 may be a 30% sulfuric acid gel.

Figure 2:
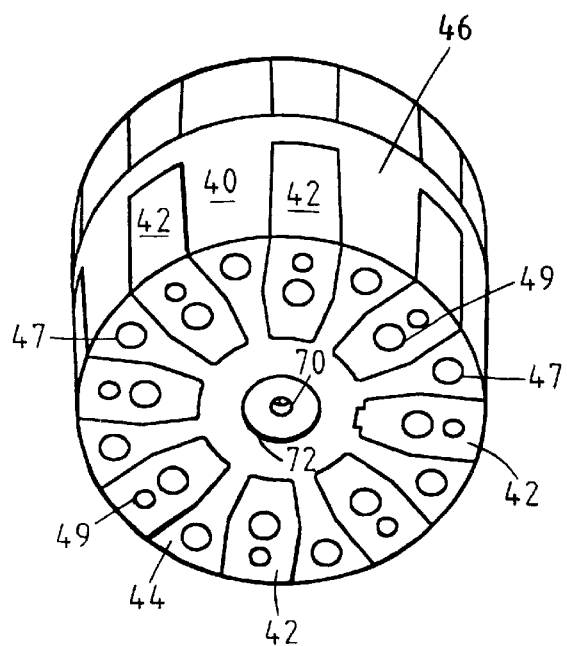
FIG. 2 is a perspective view of the bottom of the housing of the gas sensor of FIG. 1.
Figure 3:
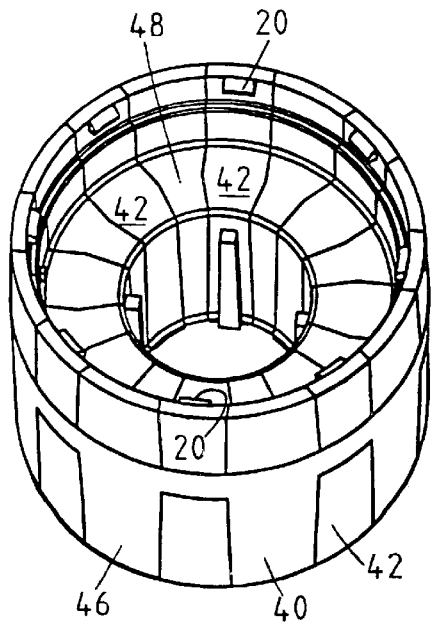
FIG. 3 is a perspective view of the top of the housing shown in FIG. 2.

FIG. 2 is a perspective view of the bottom of the cup-shaped housing 12, and FIG. 3 is a perspective view of the top of the housing 12. Referring to FIGS. 2 and 3, the housing 12 is an integral structure composed of a non-conductive plastic portion 40 and a plurality of conductive plastic portions 42 which are conductively isolated from each other by the non-conductive plastic portion 40. As shown in FIGS. 1–3, the conductive plastic portions 42 are exposed on a bottom surface 44 of the housing 12, on a curved side surface 46 of the housing 12, and on an annular interior ledge 48 (FIG. 3) of the housing 12.

The bottom surface 44 of the housing 12 has a plurality of holes 47 formed in the non-conductive housing portion 40 and a plurality of holes 49 formed in the conductive plastic portions 42. The holes 47, 49 are not necessary, but may optionally be provided to improve the injection molding process used to form the housing 12, which is described below, by making the thickness of the various portions of the housing 12 more consistent, as known by those skilled in the injection molding art. As described below, some of the holes 49 in the conductive housing portions 42 may be used to anchor electrical contact pins (not shown).

Figure 4:
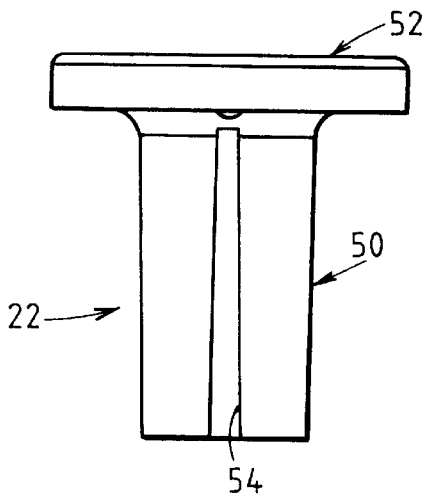
FIG. 4 is a side view of a wick support of the gas sensor of FIG. 1.
Figure 5:
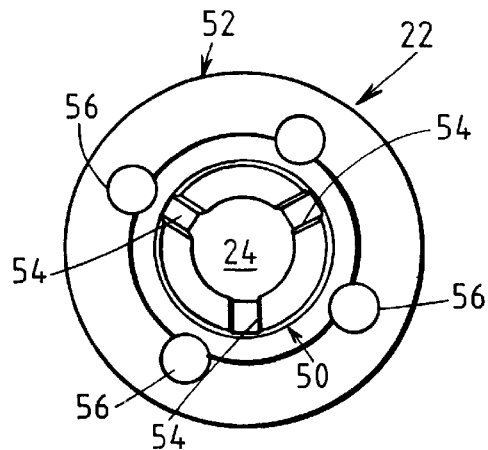
FIG. 5 is a bottom view of the wick support of FIG. 4.

FIG. 4 is a side view of the wick support 22, and FIG. 5 is a bottom view of the wick support 22. Referring to FIGS. 4 and 5, the wick support 22 has a elongate stem 50 integrally formed with an upper cylindrically shaped portion 52. The stem 50 is hollow, having the bore 24 formed therein to accommodate the wick portion 26. The stem 50 may be provided with a plurality of elongate slots 54 to allow the gas-sensing agent 16 to come into contact with and fluidly impregnate the wick portion 26. The upper portion 52 of the wick support 50 may have a plurality of holes 56 formed therein to allow the gas-sensing agent 16 to come into direct contact with the flat wick portion 28 when the gas sensor 10 is turned over or tipped onto its side.

For the satisfactory operation of the gas sensor 10, it is generally required that the receptacle 14 has a minimum ratio of air to gas-sensing agent 16, such as a 12:1 ratio of air to gas-sensing agent 16. For satisfactory operation, the wick 26, 28 should be completely impregnated with gas-sensing reagent 16. Generally, the smallest volume of gas-sensing agent 16 required is that which will completely fill the wick 26, 28 at the lowest humidity, e.g 5% humidity (since the volume of gas-sensing agent 16 may decrease during low humidity since moisture within the receptacle 14 may be lost to the atmosphere outside). Thus, if the volume of the wick 26, 28 is made smaller, so that it can be fully impregnated with a smaller amount of gas-sensing agent 16, the size of the receptacle 14, and thus the gas sensor 10, can be reduced.

With the structure of the wick support 22, a relatively small or low-volume wick 26, 28 may be used. The inside diameter of the bore 24 of the wick support 22 may be made quite small, such as one-eighth of an inch or less, so that the volume of the wick 26 disposed in the bore 24 is also quite small. The flat wick 28 may be made very thin in order to reduce or minimize the volume of the wick 26, 28. With the dimensions of the wick 26, 28 noted above, the wick 26, 28 may be completely impregnated with about 0.5 milliliters of gas-sensing agent 16.

Figure 6:
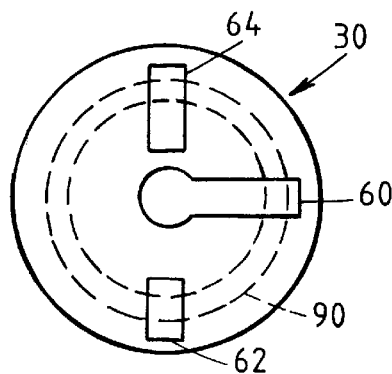
FIG. 6 illustrates an electrode support sheet of the gas sensor of FIG. 1.

Referring to FIG. 6, the electrode support sheet 30 has a plurality of electrodes formed thereon, which may include a working electrode 60, a reference electrode 62, and a counter electrode 64. The electrodes 60, 62, 64 are formed on the bottom of the sheet 30 so that they face the conductive housing portions 42 on the interior ledge 48 (FIG. 3) of the housing 12.

When the electrode support sheet 30 is placed within the housing 12, each of the electrodes 60, 62, 64 of the electrode support sheet 30 is aligned and makes conductive contact with a respective one of the conductive housing portions 42 on the interior ledge 48 of the housing 12. The electrode support sheet 30 may be provided with an alignment mechanism, such as one or more tabs (not shown), to ensure that the electrodes 60, 62, 64 are accurately aligned with the conductive housing portions 42. It should be noted that the support sheet 30 could be provided with a different number of electrodes than three and that the incorporation of eight conductive housing portions 42 would allow the use of up to eight electrodes.

Fabrication of Housing

The cup-shaped housing 12 may be formed via a conventional dual-injection molding process described as follows. First, the housing 12 without the conductive portions 42 may be injection-molded in a first mold with a non-conductive plastic, such as polypropylene. The result of the first mold will be a housing portion 12 as shown in FIGS. 2–3, but with air being present where the conductive portions 42 are shown. The housing portion 12 may then be placed in a second mold, and the conductive portions 42 may be injection-molded with a conductive plastic, such as polypropylene having carbon or other conductive fragments melted therein. The result of this conventional dual-molding process is the housing 12 shown in FIGS. 2–3 in which the non-conductive portion 40 and the conductive portions 42 together form a unitary construction.

Fabrication of Electrode Support Sheet

The electrode support sheet 30 may be fabricated from a porous PTFE substrate commercially available from Norton Performance Plastics (e.g. Part Number D996006—Zitex G110). To form the substrate, a circle is cut from the PTFE material, the circle being at least about 30% larger than the desired size of the finished electrode support sheet 30. The PTFE sheet is then pre-shrunk by heating it in an oven heated between 280° C. to 315° C. After being pre-shrunk, the PTFE sheet is trimmed to its final desired size.

Figure 7:
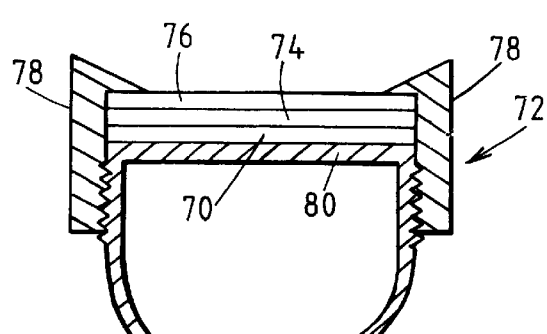
FIG. 7 illustrates a vacuum deposition apparatus that may be used in the manufacture of a gas sensor with a portion of one embodiment of the gas sensor disposed therein.

Referring to FIG. 7, the PTFE sheet formed above, which is designated by the numeral 70 in FIG. 7, is placed in a vacuum apparatus 72 below a mask having a lower mask layer 74 composed of foam and an upper mask layer 76 composed of metal. Each of the mask layers 74, 76 has a plurality of apertures (not shown) formed therein, each of the apertures having a shape that corresponds to one of the electrodes 60, 62, 64 that is to be formed. The mask layer 74 may be composed of low durometer foam which is glued to the mask layer 76, which could be composed of brass.

The vacuum apparatus 72 has a threaded cap 78, with a large aperture in the center, that holds the PTFE sheet 70 and the mask layers 74, 76 in place over a support member 80 of a vacuum funnel 82. The support member 80 has holes formed therein to allow passage of liquid therethrough. The lower end of the vacuum funnel 82 is inserted into a cork 84 tightly inserted into a vacuum chamber 86 in which a reduced pressure (i.e. lower than atmospheric pressure) is formed via an air passageway 88 connected to a vacuum pump (not shown). The vacuum apparatus 72 may be Strifil 47 mm vacuum system commercially available from Millipore (Part No. XX11-04700). The particular vacuum system used is not considered important to the invention, and various types of vacuum systems could be used.

A liquid electrode mixture is then formed by combining about 30 (±10) milligrams of platinum black catalyst, which may be fuel cell grade platinum black, Part Number S3002 commercially available from Englehard and about one gram of water, which may be Type I NCCLS/CAP type water. The water and platinum black catalyst are then mixed with a blender or mixer on high speed for four to six minutes (preferably five minutes). Then about 60 microliters of 60%

PTFE solution (which may be Part Number PTFE 30 commercially available from DuPont) is added to the mixture. The solution is then mixed for 2.5 to five (preferably three) more minutes.

The liquid electrode mixture could be simultaneously made for a plurality of electrode support sheets 30, such as seven sheets 30. In that case, the volumes of ingredients for the mixture would be multiplied by seven. Obviously, the amounts of platinum black and other ingredients used depend on the size and shape of the electrodes to be formed.

A portion of the liquid electrode mixture is then cycled through a pipette a number of times, such as three, and then using the pipette, the mixture is pipetted onto the PTFE substrate 70 through the apertures in the mask layers 74, 76 held in the vacuum apparatus 72. The electrode mixture may be pipetted onto the working electrode area first, from the center of the layer outwards, with the other electrode areas being pipetted afterwards.

A vacuum is applied (by actuating a valve, not shown) about one to 20 seconds (preferably five seconds) after the pipetting of the electrode mixture is completed. The vacuum is applied for a duration of between 20 seconds to 40 seconds (preferably 30 seconds) in order to draw the liquid through the support layer 80 while leaving the platinum black catalyst deposited in the sheet 30.

If the vacuum is left on too long, the platinum black particles will compress together resulting in a structure not porous enough. If the vacuum is not left on long enough, too much of the electrode mixture will stick to the walls of the mask layers 74, 76. The particular duration of the vacuum can be empirically determined based on the particular type of vacuum apparatus used and the magnitude of the reduced pressure drawn by the vacuum apparatus.

After the vacuum deposition of the electrode mixture, the sheet 30 is placed in a convection oven for about 90 minutes (±10 minutes) at a temperature of about 325° C. (±10° C.) to sinter the electrode mixture to complete the fabrication of the electrodes 60, 62, 64.

The method of fabricating the electrode support sheet 30 described above allows the use of an effective heat seal between the housing 12 and the electrode support sheet 30, regardless of the presence of the conductive housing portions 42 and the electrodes 30. In particular, referring to FIG. 6, use of the above method to form the electrode sheet 30 allows the formation of an effective heat seal, designated in FIG. 6 by dotted lines 90, between the entire outer periphery of the electrode sheet 30 (including portions the electrodes 60, 62, 64) and the entire periphery of the interior ledge 48 of the housing 12 (including both conductive housing portions 42 and the non-conductive housing portion 40).

Consequently, an effective heat seal may be formed between the following surfaces: 1) portions of the electrode sheet 30 on which electrodes are formed and conductive portions 42 of the housing 12; 2) portions of the electrode sheet 30 on which electrodes are formed and non-conductive portions 40 of the housing 12; 3) portions of the electrode sheet 30 on which electrodes are not formed and conductive portions 42 of the housing 12; and 4) portions of the electrode sheet 30 on which electrodes are not formed and non-conductive portions 40 of the housing 12.

The platinum black could be tested initially, by fabricating a relatively small number of sensors from the platinum black as described above, and then determining if they work. If the gas sensors operate correctly, the remaining portion of the same batch of platinum black could be used to fabricate a relatively large number of gas sensors, such as hundreds or thousands.

Overall Assembly of Gas Sensor

After the individual components of the gas sensor 10 are formed, the wick support 22 (with the wick portion 26 disposed therein) is placed in the receptacle 14 in the housing 12, the wick portion 28 is placed on the top of the wick support 22, and the electrode support sheet 30 (with the electrodes 60, 62, 64 facing downwards on it) is placed over the wick portion 28 so that the outer peripheral portion of the electrode support sheet 30 is supported by the internal ledge 48 (FIG. 3) of the housing 12.

The electrode support sheet 30 may then be sealed to the housing 12, such as by heat sealing, in a conventional manner, such as that disclosed in U.S. Pat. No. 5,744,697 to Martell, et al., which is incorporated herein by reference in its entirety. The heat seal may be performed by heating the housing 12 and electrode sheet 30 to be sealed to about 210° C. (±20° C.) in a press, such as a hydraulic press, and applying about 200 (±50) inch-pounds of force for about eight to 15 (preferably 10) seconds. It should be understood that the temperature and pressure used to form the heat seal depend on the particular size and configuration of the components 12, 30 and the size and configuration of the press, and optimal temperatures and pressures can be empirically determined.

The sealing of the electrode support sheet 30 to the housing 12 provides a substantially liquid-tight seal between the electrode support sheet 30 and the housing 12 to help prevent leakage of the gas-sensing agent 16 from the receptacle 14 and also conductively connects the portions of the electrodes 60, 62, 64 and the conductive housing portions 42 at the points where those structures make contact.

Referring to FIGS. 1 and 2, the gas-sensing agent 16 may then be introduced into the housing 12 through a hole 70 in the bottom of the housing 12 (with the housing 12 being inverted). After the gas-sensing agent 16 is added, the hole 70 may be permanently closed by heat sealing a circular seal (not shown), which may be composed of polypropylene or Teflon® for example, in a shallow countersunk bore 72 formed in the bottom of the housing 12 so that the seal covers the hole 70.

Alternative Embodiment

Figure 9:
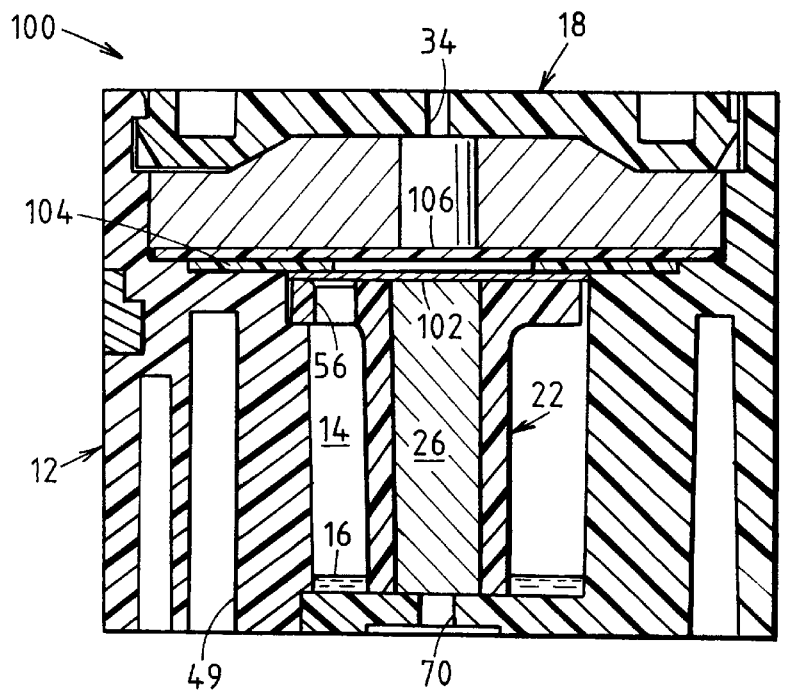
FIG. 9 is a cross-sectional view of a second embodiment of a gas sensor in accordance with the invention.
Figure 10:
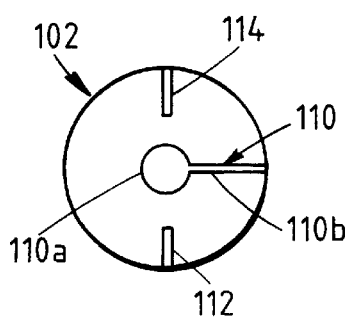
FIG. 10 illustrates a wick having a plurality of conductive paths formed thereon that may be used in the gas sensor of FIG. 9.
Figure 12:
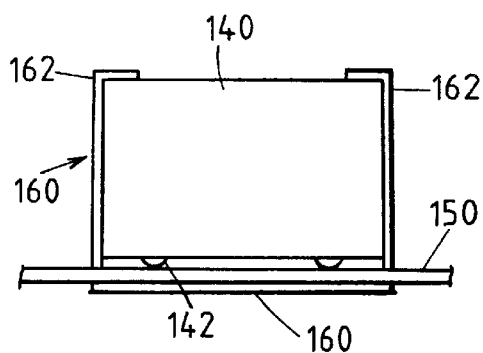
FIG. 12 illustrates a mechanism for conductively connecting a gas sensor to a printed circuit board.
Figure 11:
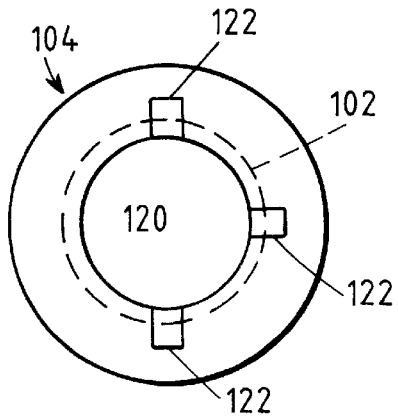
FIG. 11 illustrates a washer that may be used in the gas sensor of FIG. 9.
Figure 13:
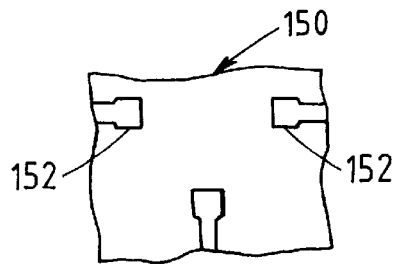
FIG. 13 illustrates a portion of a printed circuit board to which the sensor of FIG. 12 may be connected.

An alternative embodiment of a gas sensor 100 in accordance with the invention is shown in FIGS. 9–11. The gas sensor 100 is substantially the same in design as the gas sensor 10 described above, except that in the gas sensor 100, the electrodes are formed directly on the flat portion of the wick instead of on the electrode support sheet 30, and a conductive contact washer may be used to facilitate the conductive interconnection between the electrodes and the conductive housing portions 42.

Referring to FIG. 9, the gas sensor 100 incorporates a flat wick portion 102, a conductive contact washer 104 disposed directly above the flat wick 102, and a sheet 106, such as PTFE or polypropylene, disposed directly above the washer 104. As shown in FIG. 10, the flat wick 102 has a working electrode 110 having a circular center portion 110a and a thin linear portion 110b, a reference electrode 112 and a counter electrode 114 disposed thereon. The portions of the electrodes 110, 112, 114 which extend from the central portion of the flat wick 102 are much narrower than the corresponding portions of the electrodes 60, 62, 64 of the gas sensor 10 described above. Those portions of the electrodes 110, 112, 114 may be made narrower because the risk of breakage of the electrodes 110, 112, 114 is significantly reduced or eliminated because they are disposed on the wick 102, which does not expand and contract with temperature as does a PTFE sheet. By making the electrodes 110, 112, 114 narrower, the amount of costly materials (e.g. platinum) used to make the electrodes 110, 112, 114 can be significantly reduced.

Figure 8:
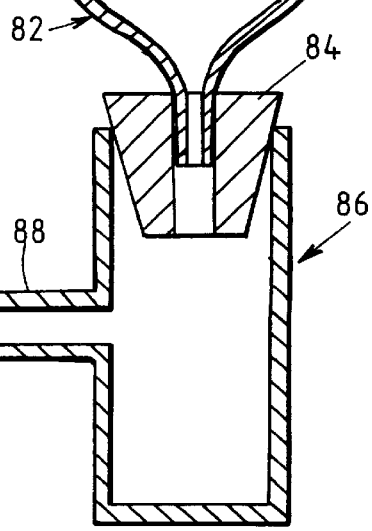

The electrodes 110, 112, 114 may be formed on the flat wick 102 by the following vacuum deposition process. Referring to FIG. 8, the flat wick 102 may have a two-piece construction, with an upper layer 102a on which the electrodes 110, 112, 114 are to be formed and a lower layer 102b. The wick layers 102a, 102b are placed on the support member 80 of the vacuum funnel 82 of the vacuum deposition apparatus, with a mask 116 having a plurality of apertures formed therein with the desired electrode pattern disposed on top of the wick layer 102a. The wick layer 102a may comprise Type GF/B glass filter paper commercially available from Whatman, and the wick layer 102b may comprise Whatman Type GF/F glass filter paper, which is softer and less rigid than the Type GF/B paper.

A liquid electrode mixture is then formed by combining about 12 (±4) milligrams of platinum black catalyst, which may be fuel cell grade platinum black, Part Number S3002 commercially available from Englehard and about 0.775 (±0.025) grams of water, which may be Type I NCCLS/CAP type water. The water and platinum black catalyst are then mixed with a blender or mixer on high speed for four to six minutes (preferably five minutes). Then about 50 microliters (±10) of 10% PTFE solution (which may be Part Number PTFE 30 commercially available from DuPont) is added to the mixture. The solution is then mixed for 2.5 to five (preferably three) more minutes. The above mixture is enough for the formation of three sets of electrodes. Obviously, the amounts of platinum black and other ingredients used depend on the size and shape of the electrodes to be formed.

A portion of the liquid electrode mixture is then cycled through a pipette a number of times, and then using the pipette, the mixture is pipetted onto the filter layer 102a through the apertures in the mask layer 116. A vacuum is applied after the pipetting of the electrode mixture is completed. After the vacuum deposition of the electrode mixture, the electrodes 110, 112, 114 are allowed to dry for at least five minutes while the layers 102a, 102b, 116 remain clamped to the support member 80. The layers 102a, 102b are then removed from the vacuum funnel 82 and sintered in a convection oven for about 90 minutes (±10 minutes) at a temperature of about 325° C. (±10° C.).

In the above process, electrodes may be vacuum deposited on multiple wicks 102 by providing a larger mask having multiple electrode patterns formed therein and by using larger sheets of wick material during the vacuum deposition process, which larger sheets can later be cut to separate them into separate wicks, each having its own set of electrodes formed thereon.

Referring to FIG. 11, the washer 104 has a central hole 120 and a plurality of conductive portions 122 disposed thereon. Each of the conductive portions 122 is positioned to coincide and partially overlap the outer portion of a respective one of each of the electrodes 110, 112, 114. To that end, the diameter of the hole 120 of the washer 104 is smaller than the outer diameter of the flat wick 102 (shown by a dotted line in FIG. 11), and each of the conductive portions 122 extends outwardly beyond the outer edge of the flat wick 102. The washer 104 may comprise a plastic material, such as PTFE for example, and the conductive portions may comprise metal or conductive plastic.

Referring to FIG. 9, to assemble the gas sensor 100, the wick layers 102a, 102b are placed on top of the wick support 22, with the electrodes 110, 112, 114 formed on the wick layer 102a facing upwards. The wick layer 102a should be oriented so that each of the electrodes 110, 112, 114 is disposed directly adjacent one of the conductive housing portions 42 (FIG. 3) of the interior ledge 48 of the housing 12.

The washer 104 is then placed over the wick layer 102b, with the conductive portions 122 of the washer 104 facing downwards and so that each of the conductive portions 122 partially overlaps one of the electrodes 110, 112, 114 of the wick layer 102b and also partially overlaps one of the conductive housing portions 42 of the interior ledge 48, so that each of the electrodes 110, 112, 114 of the wick layer 102 is in conductive contact with one of the conductive housing portions 42 of the interior ledge 48 of the housing 12.

With the wick 102 and the washer 104 so positioned, the sheet 106 is placed over them, and that assembly is subjected to a heating and pressing operation, such as described above, to bond the layer 106 and/or layer 104 to the housing 12.

Other ways of conductively connecting the electrodes 110, 112, 114 of the wick 102 could be utilized. The washer 104 could be omitted, and the conductive connections could be made by separate wires or other conductive members. The conductive connections could be made simply by subjecting the assembly (without the washer 104) to heat and pressure so that the conductive housing portions 42 would melt and come into conductive contact with the electrodes 110, 112, 114 on the flat wick 102.

Installation of Sensor

FIGS. 12–15 illustrate the installation of a gas sensor 140 (schematically shown) to a substrate 150, such as a printed circuit board. The gas sensor 140 may be the gas sensor 10 described above, the gas sensor 100 described above, or a gas sensor of another design.

Referring to FIGS. 12–15, the gas sensor 140 may have a plurality of conductive bumps 142 formed on its lower surface. Where the gas sensor 140 is provided with a housing composed of a plurality of conductive housing portions like the housing portions 42 described above, each of the bumps 142 may be integrally formed with one of the conductive housing portions. Each of the conductive bumps 142 is spaced to correspond to the spacing of a plurality of conductive contact pads 152 (FIG. 13), such as copper pads, plated or otherwise formed on the substrate 150. Consequently, when the gas sensor 140 is coupled to the substrate 150, each of the bumps 142 is conductively connected to one of the conductive contact pads 152.

The gas sensor 140 may be held in place on the substrate 150 by any means, such as a C-shaped metal spring 160 having a plurality of arms 162, each of which passes through a respective hole (not shown) formed in the substrate 150.

The conductive connection between the conductive bumps 142 (or other conductive portions of the gas sensor 140) may be enhanced by applying a conductive agent to portions of the gas sensor 140 and by having the contact pads 152 make conductive contact with the conductive agent. The use of a conductive agent will decrease the resistance between the conductive portions of the gas sensor 140 and the contact pads 152.

Figure 15:
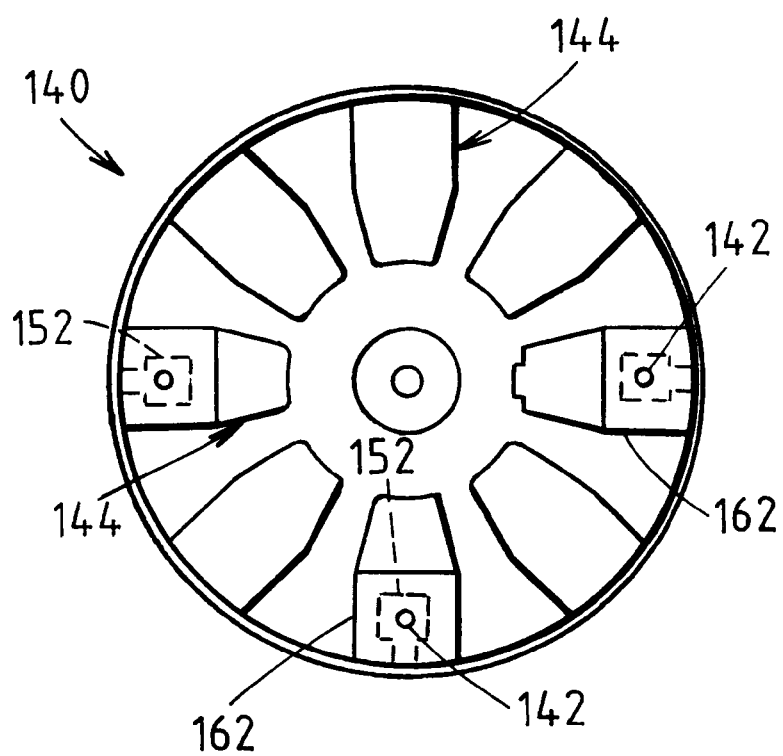
FIG. 15 illustrates a bottom portion of a gas sensor having conductive coatings disposed thereon.

FIG. 15 illustrates one example of the application of a conductive agent to the bottom of the gas sensor 140. Referring to FIG. 15, the bottom of the gas sensor 140 is shown to have eight radially disposed conductive housing portions 144. Three of the conductive housing portions 144 are shown to have a conductive agent applied to a generally square area 162 overlying the conductive housing portion 144.

Each of the three square areas 162 is larger than (at least twice as large as) the area at which each of the conductive contact pads 152 makes physical contact with the conductive bumps 142. If the bottom of the gas sensor 140 does not have conductive bumps 142, each of the three square areas 162 would be larger than (at least twice as large as) the area at which each of the conductive contact pads 152 makes physical contact with the conductive housing portions 144.

The conductive agent may be sprayed onto or otherwise applied to the areas 162, or areas having different shapes. For example, the conductive agent may be applied to the entire surface of each of a number of the conductive housing portions 144.

The conductive agent may comprise a mixture of conductive ink and an adhesive, and may also include a liquid thinning agent. For example, the conductive agent may comprise a mixture of about 15% to about 25% (preferably 20%) by volume of a conductive ink, about 15% to about 25% (preferably 20%) by volume of an adhesive, and about 50% to about 70% (preferably 60%) by volume of a thinner.

One example of a conductive ink that could be used in the conductive agent is a silver-filled polymer ink, No. 114-01, commercially available from Creative Materials, Inc. That silver ink is composed of a polyester resin (6–13% by weight), ethanol 2-butoxy acetate (15–25% by weight), 4-hydroxyl-4-methyl-2-pentanone (10–15% by weight), silver (55–70% by weight), and gamma amino propyl triethoxy silane (<2% by weight).

One example of an adhesive that could be used in the conductive agent is X17 adhesive commercially available from Master Bond, Inc. That adhesive may be composed of xylene (50% y weight) and acetone (50% by weight) and may also include modified olefin elastomer. One example of a suitable thinning agent that could be used in the conductive agent is thinner #113-12 commercially available from Creative Materials. That thinner is composed of 2-butoxyethyl acetate (95–98% by weight) and gamma amino propyl triethoxy silane (<5% by weight).

The conductive agent may be prepared by mixing the above three ingredients for a duration, such as at least about 10 minutes, applying the conductive agent (while stirring the agent continuously) to the gas sensor via an airbrush or other spray device, and then drying the conductive agent by placing the gas sensor 140 in an oven at a temperature of between 120–160° F. (preferably 140° F.) for a minimum drying time, such as 20 minutes.

Figure 14:
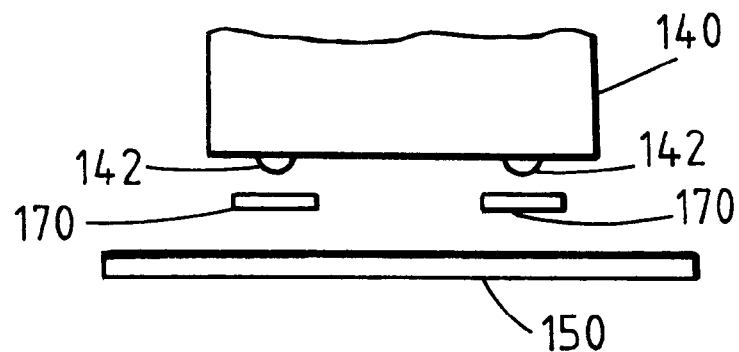
FIG. 14 is an exploded side view illustrating an alternative manner of connecting a gas sensor to a printed circuit board.

Referring to FIG. 14, to further enhance the conductive connection of the gas sensor 140 to the substrate 150, a plurality of conductive pads 170 may be utilized, with each pad 170 being disposed between one of the conductive bumps 142 and one of the conductive contact pads 152. If the gas sensor 140 does not have conductive bumps 142, each of the conductive pads 170 could be placed between one of the conductive housing portions 144 (FIG. 15) and one of the contact pads 152. One example of a conductive pad that could be used is a metallic fiber pad, such as a nickel-copper non-woven polyester fabric pad, manufactured by Monsanto and marketed as Product No. 3027-217 under the trade name Flectron®.

As an alternative manner of connecting the gas sensor 140 to the substrate 150, metal pins (not shown) could be used.

Each of the metal pins could be heated and then inserted into a hole in the bottom of the gas sensor 140, such as one of the holes 49 of the gas sensor 10 shown in FIG. 2, so that the housing would partially melt and then re-harden, thus permanently bonding the pin to the gas sensor 140. Still another way of connecting the gas sensor 140 to the substrate could utilize conductive tape having a first side on which an adhesive is disposed and a second side on which a fine steel wool or other conductive material is disposed.

Operation

In operation of the gas sensors 10, 100, to detect a gas, a constant voltage is placed between the working electrode and the reference electrode via a pair of the conductive housing portions 42 that are conductively connected to the electrodes. Then, upon the presence of the gas being detected through the sensing hole 34, an electric current will be induced between the working electrode and the counter electrode, which current can be detected and measured by a conventional current sensing circuit (not shown) attached to the conductive housing portions 42 conductively coupled to the electrodes.

Numerous modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A gas sensor assembly comprising:
    a housing having a receptacle formed therein, said housing having a non-conductive housing portion and a plurality of conductive housing portions, each of said conductive housing portions being conductively separated from each other, said conductive housing portions being composed of a conductive plastic material;
    a gas-sensing agent disposed in said receptacle;
    a plurality of electrodes disposed in conductive contact with said gas-sensing agent;
    a conductive agent disposed on an area on a first of said conductive housing portions;
    a conductive agent disposed on an area on a second of said conductive housing portions;
    a first conductor disposed in conductive contact with said conductive agent on said area on said first conductive housing portion; and
    a second conductor disposed in conductive contact with said conductive agent on said area on said second conductive housing portion,
    wherein said conductive agent disposed on said areas on said conductive housing portions comprises a sprayed-on conductive ink coating.

2. A gas sensor assembly comprising:
    a housing having a receptacle formed therein, said housing having a non-conductive housing portion and a plurality of conductive housing portions, each of said conductive housing portions being conductively separated from each other, said conductive housing portions being composed of a conductive plastic material;
    a gas-sensing agent disposed in said receptacle;
    a plurality of electrodes disposed in conductive contact with said gas-sensing agent;

a conductive agent disposed on an area on a first of said conductive housing portions;

a conductive agent disposed on an area on a second of said conductive housing portions;

a first conductor disposed in conductive contact with said conductive agent on said area on said first conductive housing portion; and a second conductor disposed in conductive contact with said conductive agent on said area on said second conductive housing portion, wherein said conductive agent disposed on said areas on said conductive housing portions comprises a mixture of conductive ink and an adhesive.

3. A gas sensor assembly comprising:

a housing having a receptacle formed therein, said housing having a non-conductive housing portion and a plurality of conductive housing portions, each of said conductive housing portions being conductively separated from each other, said conductive housing portions being composed of a conductive plastic material;

a gas-sensing agent disposed in said receptacle;

a plurality of electrodes disposed in conductive contact with said gas-sensing agent;

a conductive agent disposed on an area on a first of said conductive housing portions;

a conductive agent disposed on an area on a second of said conductive housing portions;

a first conductor disposed in conductive contact with said conductive agent on said area on said first conductive housing portion; and a second conductor disposed in conductive contact with said conductive agent on said area on said second conductive housing portion, wherein said conductive agent disposed on said areas on said conductive housing portions comprises a mixture of conductive ink, an adhesive, and a thinner.

4. A gas sensor assembly comprising:

a housing having a receptacle formed therein, said housing having a non-conductive housing portion and a plurality of conductive housing portions, each of said conductive housing portions being conductively separated from each other, said conductive housing portions being composed of a conductive plastic material;

a gas-sensing agent disposed in said receptacle;

a plurality of electrodes disposed in conductive contact with said gas-sensing agent;

a conductive agent disposed on an area on a first of said conductive housing portions;

a conductive agent disposed on an area on a second of said conductive housing portions;

a first conductor disposed in conductive contact with said conductive agent on said area on said first conductive housing portion; and a second conductor disposed in conductive contact with said conductive agent on said area on said second conductive housing portion, wherein said conductive agent disposed on said areas on said conductive housing portions comprises a mixture of about 15% to about 25% by volume of a conductive ink, about 15% to about 25% by volume of an adhesive, and about 50% to about 70% by volume of a thinner.

5. A method of forming a gas sensor assembly having a housing with a non-conductive housing portion and a plurality of conductive housing portions composed of conductive plastic material, said method comprising the steps of:

(a) forming said housing to have said non-conductive housing portion and said conductive housing portions;

(b) applying a conductive agent to an area on a first of said conductive housing portions and to an area on a second of said conductive housing portions by applying a conductive agent comprising a mixture of a conductive ink and an adhesive to an area on a first of said conductive housing portions and to an area on a second of said conductive housing portions;

(c) placing a contact surface of a first conductor in conductive contact with said conductive agent on said area on said first conductive housing portion, said first conductor making contact with said first conductive housing portion at a first contact area; and (d) placing a contact surface of a second conductor in conductive contact with said conductive agent on said area on said second conductive housing portion, said second conductor making contact with said second conductive housing portion at a second contact area.

6. A method of forming a gas sensor assembly having a housing with a non-conductive housing portion and a plurality of conductive housing portions composed of conductive plastic material, said method comprising the steps of:

(a) forming said housing to have said non-conductive housing portion and said conductive housing portions;

(b) applying a conductive agent to an area on a first of said conductive housing portions and to an area on a second of said conductive housing portions by (b1) applying said conductive agent to an area on said first conductive housing portion having a surface area of at least about twice the surface area of said first contact area and (b2) applying said conductive agent to an area on said second conductive housing portion having a surface area of at least about twice the surface area of said second contact area;

(c) placing a contact surface of a first conductor in conductive contact with said conductive agent on said area on said first conductive housing portion, said first conductor making contact with said first conductive housing portion at a first contact area; and (d) placing a contact surface of a second conductor in conductive contact with said conductive agent on said area on said second conductive housing portion, said second conductor making contact with said second conductive housing portion at a second contact area.

7. A method of forming a gas sensor assembly having a housing with a non-conductive housing portion and a plurality of conductive housing portions composed of conductive plastic material, said method comprising the steps of:

(a) forming said housing to have said non-conductive housing portion and said conductive housing portions;

(b) applying a conductive agent to an area on a first of said conductive housing portions and to an area on a second of said conductive housing portions by spraying said conductive agent on said areas on said first and second conductive housing portions;

(c) placing a contact surface of a first conductor in conductive contact with said conductive agent on said area on said first conductive housing portion, said first conductor making contact with said first conductive housing portion at a first contact area; and (d) placing a contact surface of a second conductor in conductive contact with said conductive agent on said area on said second conductive housing portion, said second conductor making contact with said second conductive housing portion at a second contact area.

* * * * *